United States Patent [19]
Tornier

[11] Patent Number: 5,405,399
[45] Date of Patent: Apr. 11, 1995

[54] TOTAL PROSTHESIS FOR THE METACARPO-PHALANGEAL JOINT

[75] Inventor: Alain Tornier, Saint-Ismier, France

[73] Assignee: Etablissements Tornier, Saint-Ismier, France

[21] Appl. No.: 59,362

[22] Filed: May 11, 1993

[30] Foreign Application Priority Data

May 25, 1992 [FR] France ................ 92 06588

[51] Int. Cl.⁶ .............................................. A61F 2/42
[52] U.S. Cl. ............................................ 623/21; 623/18
[58] Field of Search ........................ 623/18, 21, 20, 23

[56] References Cited

U.S. PATENT DOCUMENTS

| | | | |
|---|---|---|---|
| 4,242,759 | 1/1981 | White | 623/21 |
| 4,718,914 | 1/1988 | Frey et al. | 623/23 |
| 4,725,280 | 2/1988 | Laure | 623/21 |
| 5,219,362 | 6/1993 | Tuke et al. | 623/16 |
| 5,226,916 | 7/1993 | Goodfellow et al. | 623/20 |

OTHER PUBLICATIONS

Orthopaedics Catalog, Richards Manufacturing Co, Inc., Memphis, Tenn., 1981.

Primary Examiner—David Isabella
Assistant Examiner—Debra S. Brittingham
Attorney, Agent, or Firm—Dowell & Dowell

[57] ABSTRACT

A total prothesis for the metacarpo-phalangeal joint which includes a first element for anchoring in the phalangeal diaphysis having a tapering head provided with at least two articular surfaces of concave profile and a second element for anchoring in the metacarpo diaphysis having a head including at least two separate articular surfaces. One of the articular surfaces of the second element is generally convex and the other articular surface includes an arcuate ridge which extends outwardly relative to the convex articular surface and toward the articular surfaces of the first element.

11 Claims, 5 Drawing Sheets

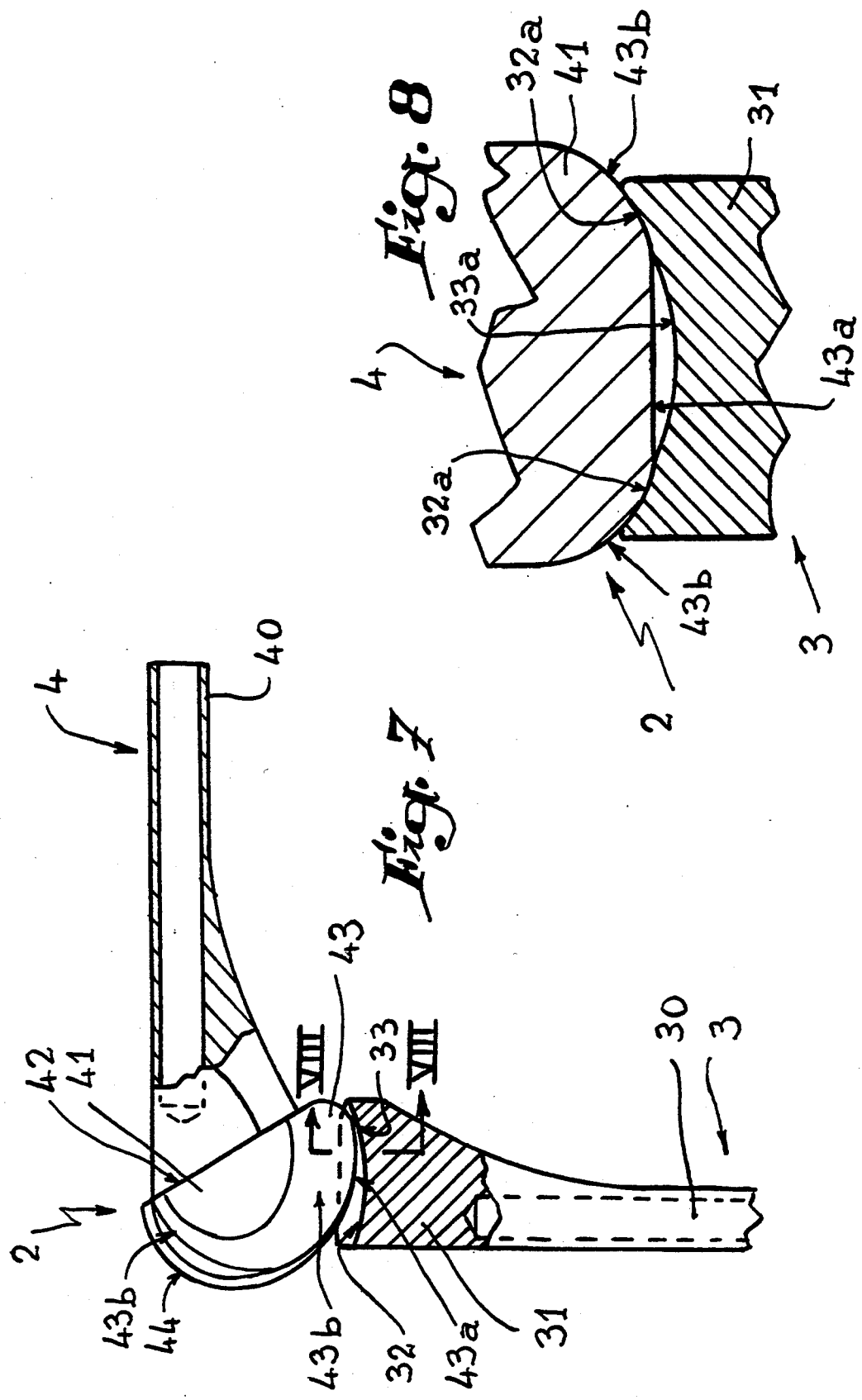

TOTAL PROSTHESIS FOR THE METACARPO-PHALANGEAL JOINT

FIELD OF THE INVENTION

BACKGROUND OF THE INVENTION

The present invention relates to a total prosthesis for the metacarpo-phalangeal joint of each finger of a hand, which comprises two distinct elements coming into contact with each other with the osseous, ligamentary or muscular structure remaining in place.

HISTORY OF THE RELATED ART

Prostheses of this type are known, which generally comprise a block of elastic material implanted in the osseous diaphyses to replace the damaged part of the metacarpo-phalangeal joint. Such blocks are shaped so as to reduce as much as possible the stresses due to friction, so that the movement of the prosthesis is based on the elastic characteristics of the material used.

Such prostheses present certain drawbacks concerning both the life duration of the elastic blocks, which is notably short, and the stresses that these blocks generate on the joint due to their rudimentary design.

Metal prostheses are also known which assimilate the metacarpo-phalangeal joint to a joint of the hinge type. Such prostheses are not capable of reproducing perfectly the normal kinematics of the joint, which brings about considerable complications. Such complications are generally due to the stresses that the prosthesis generates on the joint and which are translated by a loosening of the body of the prosthesis.

It is a principal object of the present invention to overcome these drawbacks by providing a prosthesis which perfectly reproduces the movement of the metacarpo-phalangeal joint.

SUMMARY OF THE INVENTION

The total prosthesis according to the invention comprises:

a first element including a shank for anchoring in the phalangeal diaphysis and a tapering head provided with at least two articular surfaces of concave profile each presenting a distinct radius of curvature in barrel form;

and a second element provided with a shank for anchoring in the metacarpal diaphysis and a head having an outer profile with at least two distinct articular surfaces respectively defining a first radius of curvature of circular type, whose edges are rounded, and a second radius of curvature in the form of a peak in portion of sphere originating in the lower part of the head and in the middle of the first radius of curvature.

Another object of the invention consists in producing a non-stressed total prosthesis which enables the whole of the osseous, ligamentary or muscular structure remaining in place to guide the movement of the metacarpo-phalangeal joint.

The total prosthesis of the metacarpo-phalangeal joint may be used with or without cement. In addition, the two elements constituting the total prosthesis respectively include articular surfaces which include a plurality of radii of curvature and distinct profiles, so that the kinematics differ depending on the angular positions of the two elements with respect to each other.

BRIEF DESCRIPTION OF THE DRAWINGS

The invention will be more readily understood on reading the following description with reference to the accompanying drawings, in which:

FIG. 7 is a side view in partial section showing the total prosthesis in a position of phalangeal flexion inclined by an angle of 90° with respect to a horizontal plane.

FIG. 8 is an enlarged partial section along lines VIII—VIII of FIG. 7 showing the articular surfaces of the two elements which are in contact in position of inclined flexion according to FIG. 7.

DESCRIPTION OF THE PREFERRED EMBODIMENT

Figure 1:
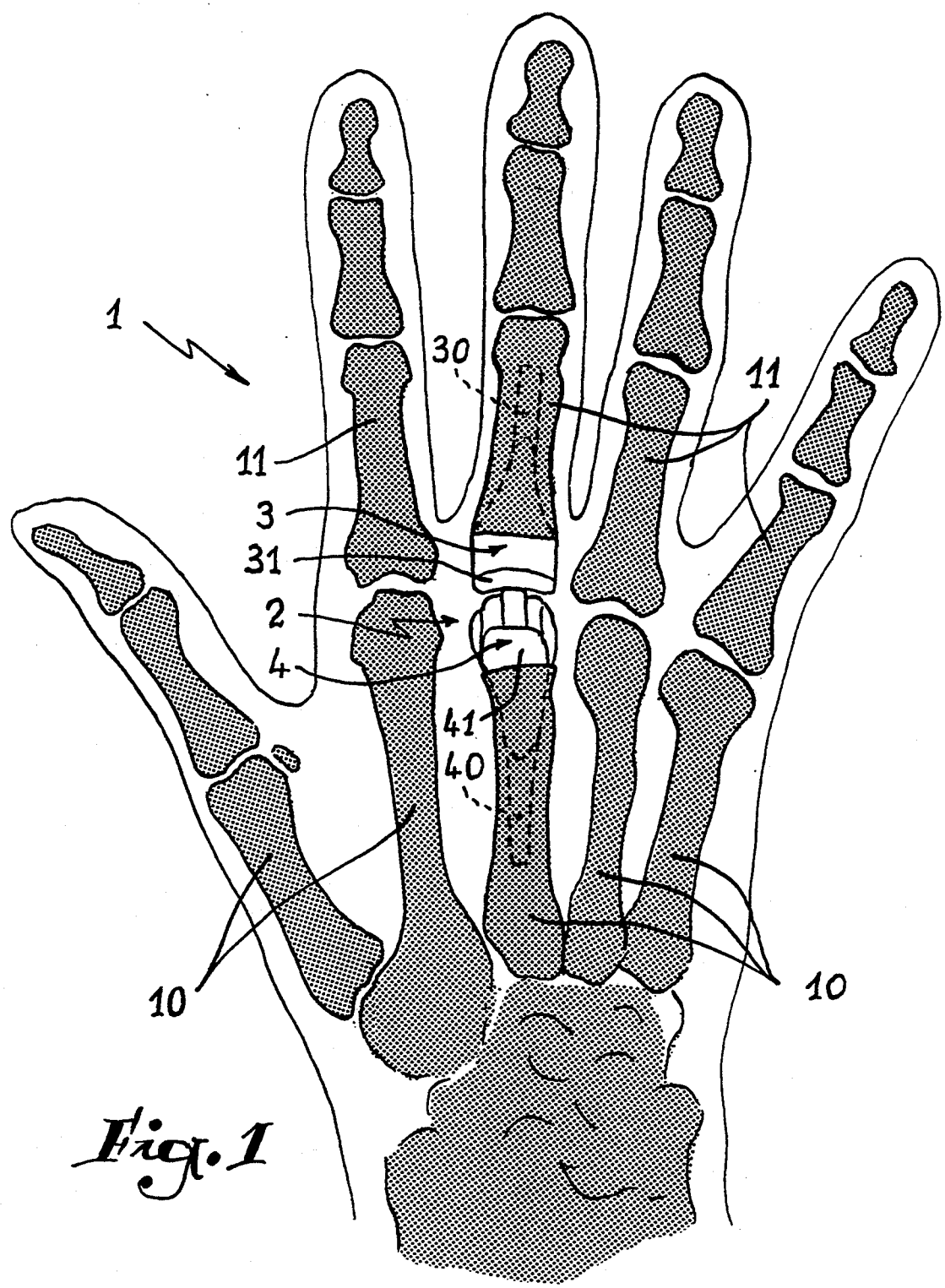
FIG. 1 is an overall view showing the bones constituting a right hand of which one of the metacarpo-phalangeal joints is composed of a total prosthesis according to the invention.

Referring now to the drawings, FIG. 1 shows a right hand 1 of which the metacarpo-phalangeal joints are constituted by metacarpal bones 10 and phalanges 11, one of the latter being composed of a total prosthesis 2.

The total prosthesis comprises a first element 3 and a second element 4 which are respectively anchored in the phalangeal and metacarpal diaphysis. These two elements are independent of each other and are in contact solely via their articular surfaces which will be better distinguished hereinafter.

Figure 2:
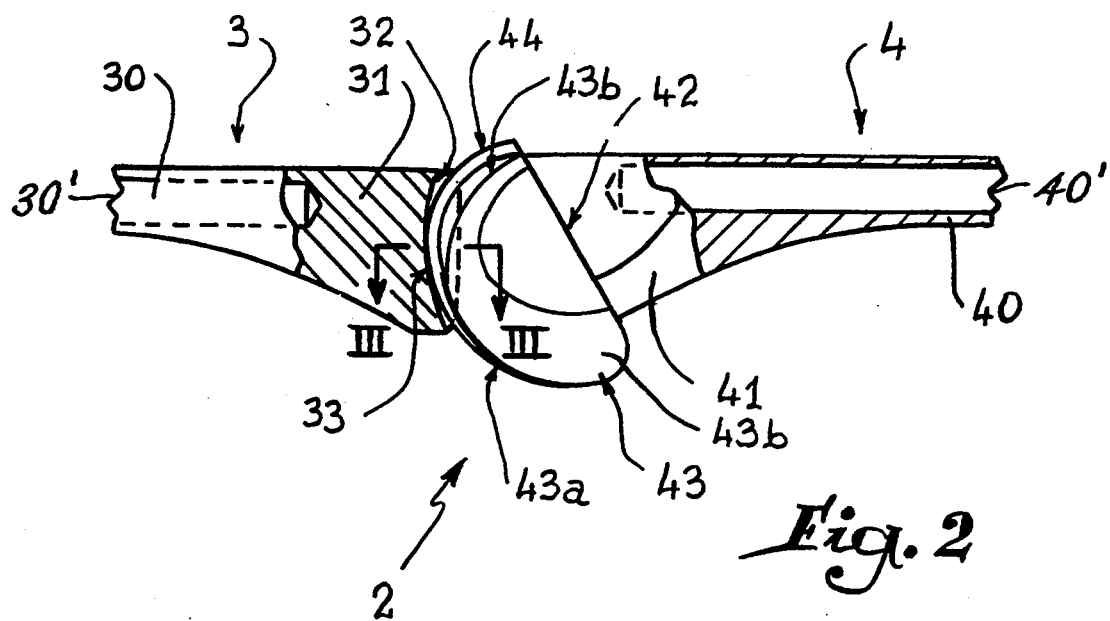
FIG. 2 is a side view in partial section illustrating the arrangement of the total prosthesis in position of extension.

As illustrated in FIG. 2, the first element 3 of the prosthesis comprises a hollow shank 30 having a tulip-shaped profile i.e. generally hollow with spaced pointed edges 30' extending from the end thereof to allow anchoring thereof in the phalangeal diaphysis. This shank 30 is adapted to the internal morphology of the bone 11 and may be provided with a device for promoting anchoring by osseous regrowth.

At one of its ends, the shank 30 is provided with a tapering head 31 forming the articular part of the phalanx. This tapering head 31 includes two distinct articular surfaces 32 and 33 of concave profile so as to reproduce the surfaces of the phalangeal bone 11. The articular surfaces 32, 33 respectively defining a radius of curvature 32a and 33a in the form of a segment of the surface of a barrell, i.e. generally concave in configuration from top to bottom and from side to side as shown in the FIGS. 2 and 3. The tapering head 31 may, for example, be added to the phalangeal shank 30 via a pin (not shown) so as to adapt to all the morphologies of a metacarpo-phalangeal joint.

The second element 4 comprises a hollow shank 40 presenting a tulip-shaped profile i.e. generally hollow with spaced pointed edges 40' extending from the end thereof, to allow anchoring thereof inside the metacarpal diaphysis of the bone 10. This shank 40 is adapted to the internal morphology of the bone 10 and may comprise a device for promoting anchoring by osseous regrowth.

At one of the ends of the shank 40 is provided a head 41 which has an outer shape capable of adapting perfectly, in all the planes, to the profile provided on the tapering head 31 of the first element 30. The head 41 includes, towards the shank 40 and on either side thereof, an inclined face 42 serving as bearing for the osseous cut made on the metacarpal articular surface. The outer surface of the head 41 is divided into two distinct articular surfaces 43 and 44 which come into contact with the articular surfaces 32 and 33 of the phalangeal head 31 so as to be adapted to the different angular positions that the total prosthesis 2 may take.

The articular surface referenced 43 has a radius of curvature of cylindrical type, 43a, whose edges are rounded in a profile 43b. The articular surface referenced 44 is disposed in the middle of the first surface 43 and presents a radius of curvature having as outer profile defined as a peak or outer ridge in a portion of a segment of a sphere. The articular surface 44 originates and is plush with the lower part of the head 41 and in the middle of the radius of curvature 43a. As shown in FIG. 2, the ridge 44 extends progressively outwardly from the articular surface 43 toward the upper part of the head 41 so the articular surface 44 divides the articular surface 43 into two equivalent portions, so as to allow only the edges having a rounded profile, 43b, to appear.

Figure 3:
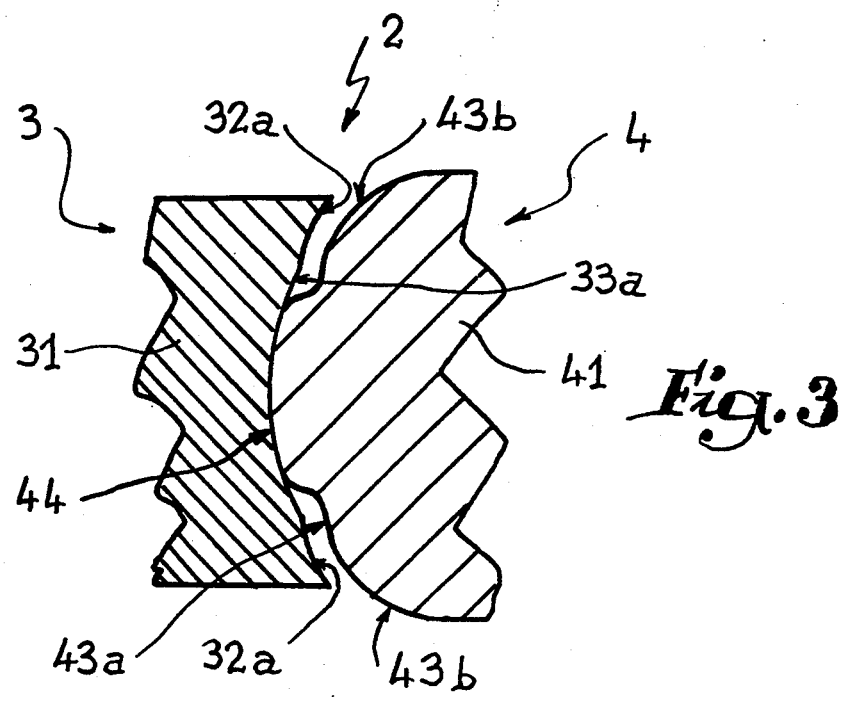
FIG. 3 is an enlarged partial section along lines III—III of FIG. 2, showing the articular surfaces of the two elements which are in contact in the position of extension.
Figure 4:
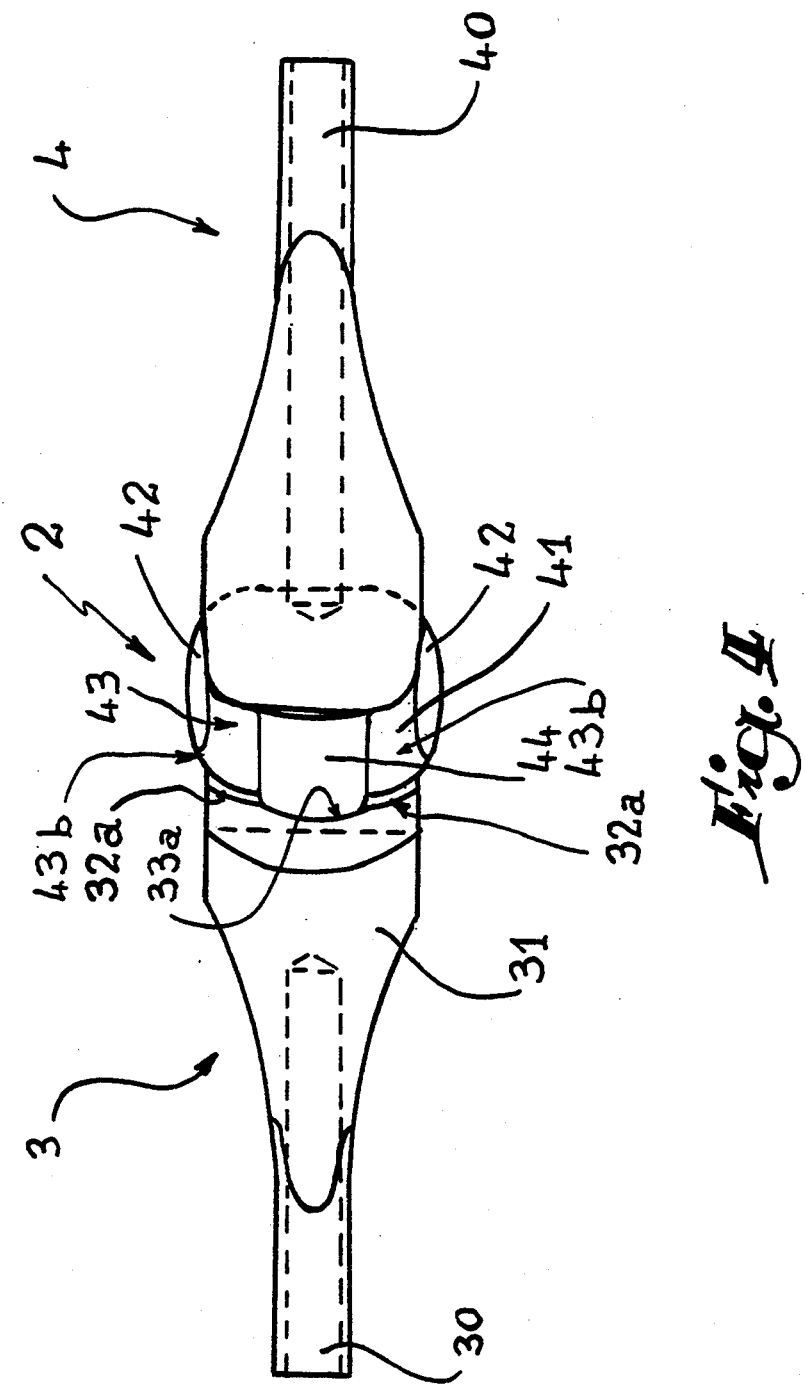
FIG. 4 is a plan view showing the total prosthesis in the same position as that of FIG. 1.

FIGS. 2, 3 and 4 show the total prosthesis 2 in position of maximum extension, i.e. when the hand 1 is for example placed flat on a horizontal or vertical surface.

FIG. 3 shows in detail the articular surfaces of the first element 3 and of the second element 4 which come into contact with each other. It will be noted that, in this position of extension, only the articular surface 44 having as outer profile a peak in a portion of a segment of a sphere and belonging to the second element 4 is in contact with the surface defined by the radius of curvature 33a of the surface 33 of the first element 3.

It will also be noted that, in this position, the first element 3, i.e. the one comprising the phalangeal shank 30, may move laterally with respect to the second element 4 which is fixed in the metacarpal diaphysis of bone 10.

Figure 5:
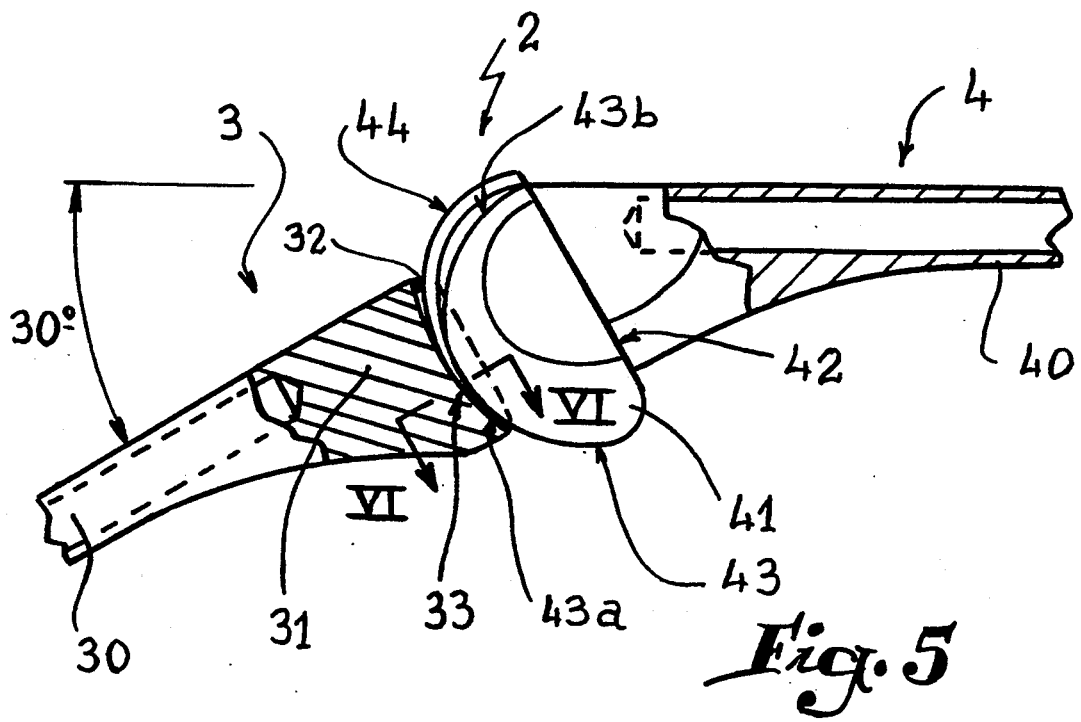
FIG. 5 is a side view similar to that of FIG. 2, but showing the total prosthesis in a position of phalangeal flexion inclined by an angle of 30° downwardly with respect to a horizontal plane.
Figure 6:
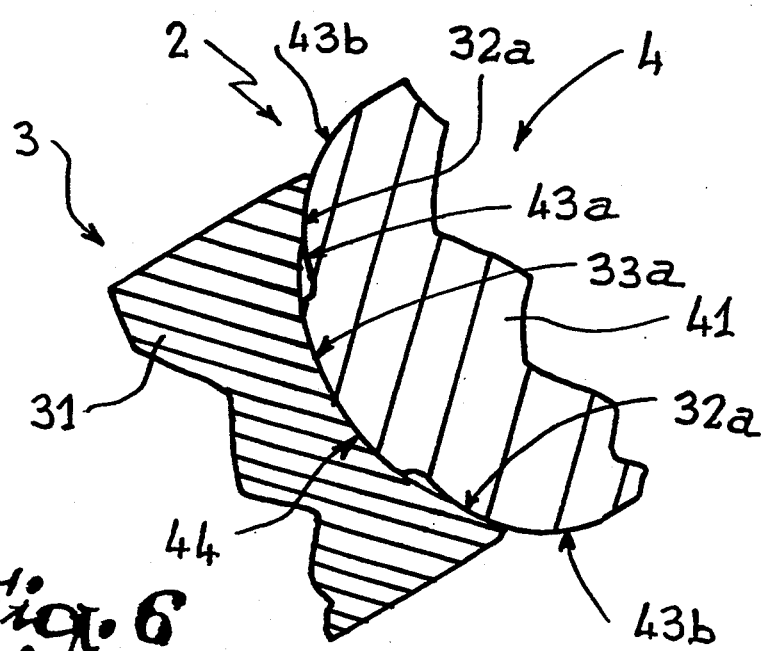
FIG. 6 is an enlarged partial section along lines VI—VI of FIG. 5 showing the articular surfaces of the two elements which are in contact in position of inclined flexion according to FIG. 5.

FIGS. 5 and 6 show the total prosthesis 2 at the beginning of its flexion, i.e. when the element 3 is inclined by an angle of 30° with respect to the second element 4 which is provided to be in a horizontal plane. It is observed that, in this position, the surfaces defined by radii of curvature 32a and 33a of element 3 are in contact, respectively, with the rounded edges 43b of the articular surface 43 and on the other hand with the articular surface 44.

It will also be observed that the beginning of the articular surface 44 in the form of a spherical peak is made complimentary with the profile of the articular surface 43 in order not to hinder the movements of flexion and of extension of the first element 3 with respect to the second element 4. In this position inclined by 30°, the lateral displacements of the first element 3 are limited, being given that the radius of curvature 32a begins to bear on the rounded edges 43b of the articular surface 43.

In FIGS. 7 and 8, the prosthesis 2 is shown in total flexion, i.e. when the first element 3 is inclined by an angle of 90° with respect to the second element 4 which is provided to be in a horizontal plane. In this position, the radius of curvature 32a of the articular surface 32 of the first element 3 is solely in contact with the articular surface 43 and more particularly with the rounded edges 43b of the radius of curvature of cylindrical type, 43a, thus preventing any lateral displacement of the first element 3 with respect to the second element 4.

It will be noted that the total prosthesis makes it possible, because of its two articular surfaces 43 and 44 coming successively into function in the course of the movement of the first element 3 with respect to the second element 4, to reproduce perfectly the movements registered in a healthy metacarpo-phalangeal joint.

It must, moreover, be understood that the foregoing description has been given only by way of example and that it in no way limits the domain of the invention which would not be exceeded by replacing the details of execution described by any other equivalents.

What is claimed is:

1. A total prothesis for the joint between a metacarpal bone and a phalangeal bone comprising;
    a first element having a first shank for anchoring in the phalangeal bone, a first head extending from said first shank and provided with at least two articular surfaces of concave profile, and having a shape of a barrel having differing radial configurations;
    and a second element having a second shank for anchoring in the metacarpal bone, a second head extending from said second shank and having at least two separate articular surfaces, said second head having upper and lower portions, a first of said at least two articular surfaces of said second head having a first radius of curvature of generally convex profile and having rounded edges, a second of said at least two articular surfaces having an arcuate ridge which is generally flush with a portion of said first articular surface of said second head, said ridge extending progressively outwardly from said first articular surface toward the upper portion of said second head; and
    said articular surfaces of said first head being in slidably opposing relationship to said articular surfaces of said second head.

2. The prosthesis of claim 1 wherein said second head includes opposite sides, an inclined face adjacent each of said opposite sides, and each of said inclined faces being oriented toward said second shank.

3. The prosthesis of claim 1 wherein said ridge is oriented so as to divide said first articular surface into first and second substantially equal portions, and said first and second portions being spaced on opposite sides of said ridge.

4. The prosthesis of claim 1 wherein in said first shank is hollow having an outer end, said outer end including a plurality of pointed edges.

5. The prosthesis of claim 1 wherein said second shank is hollow having an outer end, said outer end including a plurality of pointed edges.

6. The prosthesis of claim 1 in which said first head includes a generally central first articular surface of concave profile and a pair of second articular surfaces of concave profile on opposite sides of said first articular surface, and each of said second articular surface having generally similar radial configurations.

7. The prosthesis of claim 6 in which said first articular surface of said first element is slidingly engageable with said ridge of said second element and said second articular surfaces of said first element are slidingly engageable with said first articular surfaces of said second element on opposite sides of said ridge.

8. The prosthesis of claim 7 wherein said second head includes opposite sides, an inclined face adjacent each of said opposite sides and, each of said inclined faces being oriented toward said second shank.

9. The prosthesis of claim 8 wherein said ridge is oriented so as to divide said first articular surface into first and second substantially equal portions, and said first and second portions being spaced on opposite sides of said ridge.

10. The prosthesis of claim 9 wherein in said first shank is hollow having an outer end, said outer end including a plurality of pointed edges.

11. The prosthesis of claim 10 wherein said second shank is hollow having an outer end, said outer end including a plurality of pointed edges.

* * * * *